(12) United States Patent
Han et al.

(10) Patent No.: US 10,711,354 B2
(45) Date of Patent: Jul. 14, 2020

(54) ELECTROLYSIS APPARATUS FOR COLLECTING NITROGEN COMPOUND USING FERRIC-ETHYLENEDIAMINE TETRAACETIC ACID

(71) Applicant: KOREA ADVANCED INSTITUTE OF SCIENCE AND TECHNOLOGY, Daejeon (KR)

(72) Inventors: Jong-In Han, Daejeon (KR); Dongyeon Kim, Daejeon (KR); Nara Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/751,870

(22) PCT Filed: Dec. 16, 2015

(86) PCT No.: PCT/KR2015/013825
§ 371 (c)(1),
(2) Date: Feb. 11, 2018

(87) PCT Pub. No.: WO2017/030249
PCT Pub. Date: Feb. 23, 2017

(65) Prior Publication Data
US 2018/0230606 A1    Aug. 16, 2018

(30) Foreign Application Priority Data

Aug. 18, 2015  (KR) .................. 10-2015-0116167
Dec. 16, 2015  (KR) .................. 10-2015-0180430

(51) Int. Cl.
  C25B 1/22      (2006.01)
  C25B 11/04    (2006.01)
(Continued)

(52) U.S. Cl.
  CPC ............. C25B 1/22 (2013.01); B01D 53/326 (2013.01); B01D 53/56 (2013.01);
(Continued)

(58) Field of Classification Search
  None
  See application file for complete search history.

(56) References Cited

U.S. PATENT DOCUMENTS 1,543,357 A * 6/1925 Baur .................... C25B 1/04
                                                                205/354
4,126,529 A * 11/1978 DeBerry ............... B01D 53/60
                                                                204/526
(Continued)

FOREIGN PATENT DOCUMENTS

KR    20110101452 A    9/2011
KR    101189238 B1    10/2012
(Continued)

OTHER PUBLICATIONS

Scovazzo et al, Electrochemical Separation and Concentration of <1% Carbon Dioxide from Nitrogen, Journal of the Electrochemical Society, vol. 150, No. 5, 2003 (no month), pp. D91-D98 (Year: 2003).*

(Continued)

Primary Examiner — Harry D Wilkins, III
(74) Attorney, Agent, or Firm — Hultquist, PLLC; Steven J. Hultquist

(57) ABSTRACT

The present invention relates to an electrolysis apparatus for collecting a nitrogen compound using ferric-ethylenediaminetetraacetic acid (Fe-EDTA), and more particularly, to an electrolysis apparatus for collecting a nitrogen compound in exhaust gas by supplying electric energy to cause a redox reaction of Fe-EDTA.

17 Claims, 2 Drawing Sheets

(51) Int. Cl.
  *B01D 53/32* (2006.01)
  *B01D 53/56* (2006.01)
  *C01B 21/40* (2006.01)
  *F01N 3/08* (2006.01)
  *C07C 229/16* (2006.01)

(52) U.S. Cl.
  CPC ........ *C25B 11/0473* (2013.01); *F01N 3/0842* (2013.01); *F01N 3/0892* (2013.01); *B01D 2251/902* (2013.01); *B01D 2255/20738* (2013.01); *B01D 2257/404* (2013.01); *B01D 2258/01* (2013.01); *B01D 2258/0283* (2013.01); *B01D 2258/0291* (2013.01); *C01B 21/40* (2013.01); *C07C 229/16* (2013.01); *F01N 2240/34* (2013.01)

(56) References Cited

U.S. PATENT DOCUMENTS

| | | | | |
|---|---|---|---|---|
| 4,158,044 | A | * | 6/1979 | Takabatake ............ B01D 53/56 423/235 |
| 4,253,925 | A | * | 3/1981 | Mason ................ B01D 53/326 204/272 |
| 4,419,207 | A | * | 12/1983 | Bindon ..................... C25B 9/00 204/237 |
| 4,925,639 | A | * | 5/1990 | Stauffer ............... B01D 53/326 205/349 |
| 5,354,436 | A | | 10/1994 | Van Velzen et al. |
| 6,015,483 | A | * | 1/2000 | Plog ..................... B01D 53/326 204/265 |
| 9,567,678 | B2 | * | 2/2017 | Eltayeb ................. B01J 19/088 |
| 2005/0230269 | A1 | * | 10/2005 | Machida .............. B01D 53/326 205/763 |
| 2009/0057161 | A1 | * | 3/2009 | Aulich ...................... C05C 9/00 205/436 |
| 2010/0000876 | A1 | * | 1/2010 | Kirchoff .................. C25B 1/04 205/637 |
| 2013/0058857 | A1 | * | 3/2013 | Stern .................... B01D 53/326 423/415.1 |
| 2015/0259811 | A1 | | 9/2015 | Takeuchi |

FOREIGN PATENT DOCUMENTS

| | | |
|---|---|---|
| KR | 101366183 B1 | 2/2014 |
| KR | 101522857 B1 | 11/2014 |
| KR | 20140131401 A | 11/2014 |
| KR | 20150060978 A | 6/2015 |

OTHER PUBLICATIONS

Gambardella, NO and O2 absorption in FeII(EDTA) solutions, Thesis from Univeristy of Groningen, 2005 (no month), pp. 1-141 (Year: 2005).*

Hishinuma et al, Reversible Binding of NO to Fe(II)edta, Bulletin of the Chemical Society of Japan, vol. 52, No. 10, 1979 (no month), pp. 2863-2865 (Year: 1979).*

Juzeliunas et al, Electrochemical Study of NO Conversion from Fe(II)-EDTA-NO Complex on Pt Electrodes, Journal of the Electrochemical Society, vol. 145, No. 1, 1998 (no month), pp. 53-58 (Year: 1998).*

* cited by examiner (a) NO₂ removal process
(b) NO collection (removal) process
(c) NO separation/collection & complex regeneration process

ELECTROLYSIS APPARATUS FOR COLLECTING NITROGEN COMPOUND USING FERRIC-ETHYLENEDIAMINE TETRAACETIC ACID

CROSS-REFERENCE TO RELATED APPLICATIONS

This application is a U.S. national phase under the provisions of 35 U.S.C. § 371 of International Patent Application No. PCT/KR15/13825 filed Dec. 16, 2015, which in turn claims the priority of Korean Patent Application No. 10-2015-0116167 filed Aug. 18, 2015 and the priority of Korean Patent Application No. 10-2015-018-0430 filed Dec. 16, 2015. The disclosures of such international patent application and Korean priority patent applications are hereby incorporated herein by reference in their respective entireties, for all purposes.

TECHNICAL FIELD

The present invention relates to an electrolysis apparatus for collecting a nitrogen compound using ferric-ethylenediaminetetraacetic acid (Fe-EDTA), and more particularly, to an electrolysis apparatus for collecting a nitrogen compound in exhaust gas by supplying electric energy to cause a redox reaction of Fe-EDTA.

BACKGROUND ART

A large amount of nitrogen oxides ($NO_x$) harmful to a human body is produced in the combustion process of automobile engines and fossil fuel use facilities such as a power generation facility, an industrial boiler and an incineration facility, and the discharge of these nitrogen oxides ($NO_x$) has a significant influence on air pollution, such as acid rain, a reduced ozone layer and generation of photochemical smog.

As a process for removing them, selective catalytic reduction (SCR) and selective non-catalytic reduction (SNCR) which spray a reducing agent ($NH_3$, etc.) to a catalyst, a process using an electron beam, a pulse corona discharge process, and the like have been studied and developed. As nitrogen oxide reduction technology is developed, emissions of nitrogen oxides have been slightly decreased over the past decade, however, about 30 million tons of nitrogen oxides are still emitted annually only in the United States, and in the case of using the selective catalytic reduction (SCR) which is most widely used for removing the nitrogen oxides, an astronomical amount of about 24 billion dollars is required.

In addition, a BioDeNox process for treating nitrogen oxides ($NO_x$) using microorganisms has been newly developed and becomes popular. The BioDeNox process is the most recent technology, and allows the nitrogen oxides ($NO_x$) to be treated even at room temperature using microorganisms, unlike other processes, thereby significantly reducing energy consumption. The core of this technology is excellent selective binding capacity and binding rate of divalent ferric-ethylenediaminetetraacetic acid to nitrogen monoxide (NO), and in the course of reaction, the divalent ferric-ethylenediaminetetraacetic acid is oxidized to trivalent ferric-ethylenediaminetetraacetic acid which is an inactive form by oxygen contained in exhaust gas, and thus, a regeneration process should be necessarily included. Since the BioDeNox method uses microorganisms which may reduce trivalent iron ion in this regeneration process, the reduction rate is significantly slow, and a lot of energy and cost are consumed in treating separated nitrogen oxides ($NO_x$).

Korean Patent Registration No. 1522857 discloses a composite type selective reduction catalyst. This patent discloses a catalyst having improved purification ability at low temperature, by using a composite SCR catalyst having a bilayer structure, being coated on a carrier (substrate), in which a $V_2O_5/TiO_2$ layer is formed in an upper layer, and a metal-contained zeolite layer is formed in a lower layer, however, since vanadium and titanium which are expensive rare earth precious metals are used, it costs a lot of money for preparation.

Korean Patent Registration No. 1189238 discloses a nitrogen oxide adsorption-reduction catalyst. This patent discloses a catalyst including a carrier including Li and Al; a nitrogen oxide-adsorption element of an alkali metal, an alkali earth metal or a rare-earth element; and one or more precious metals selected from the group consisting of Pt, Pd, Ru, Ag, Au and Rh, thereby having excellent adsorption ability even before and after deterioration and before and after sulfation, however, since the catalyst uses a large amount of rare-earth precious metals, it costs a lot of money for nitrogen oxides adsorption.

Thus, the present inventors devoted extensive effort for solving the problems, and as a result, developed an electrolysis apparatus for collecting a nitrogen compound using Fe-EDTA, and as a result of performing a nitrogen oxide collecting test using the electrolysis apparatus, confirmed that the nitrogen compound in exhaust gas may be efficiently collected, with the use of expensive rare-earth elements being minimized, thereby completing the present invention.

The above information described in the Background Art is only for improving understanding of the background of the present invention, and thus, may not include information forming the prior art which is already known to a person with ordinary skill in the art to which the present invention pertains.

SUMMARY OF THE INVENTION

An object of the present invention is to provide an electrolysis apparatus for collecting a nitrogen compound.

Another object of the present invention is to provide a method of collecting a nitrogen compound using the electrolysis apparatus.

In order to achieve the above objects, the present invention provides an electrolysis apparatus for collecting a nitrogen compound, comprising (a) a reactor body comprising a compound of divalent metal ion and chelating agent therein; (b) an anode and a cathode; (c) a collection tube for collecting the nitrogen compound, comprising the anode therein; (d) a gas inlet for supplying raw material gas containing the nitrogen compound to the reactor body; and (e) an outlet for discharging gas which has been collected inside the reactor and the nitrogen compound is removed from.

The present invention also provides a method of collecting a nitrogen compound using the electrolysis apparatus, the method comprising (i) adsorbing the nitrogen compound to the compound of divalent metal ion and chelating agent by supplying raw material gas comprising a nitrogen compound to a reactor containing a compound of divalent metal ion and chelating agent; (ii) collecting discharged nitrogen compound by supplying electricity to an anode and a cathode, oxidizing the nitrogen compound-adsorbed compound of divalent metal ion and chelating agent to a compound of trivalent metal ion and chelating agent through an oxidation reaction in the anode and discharging the nitrogen compound; (iii) recovering collected nitrogen compound; and (iv) reducing oxidized compound of trivalent metal ion and chelating agent to the compound of divalent metal ion and chelating agent by electrons produced in the cathode.

DESCRIPTION OF SYMBOLS

Figure 1:
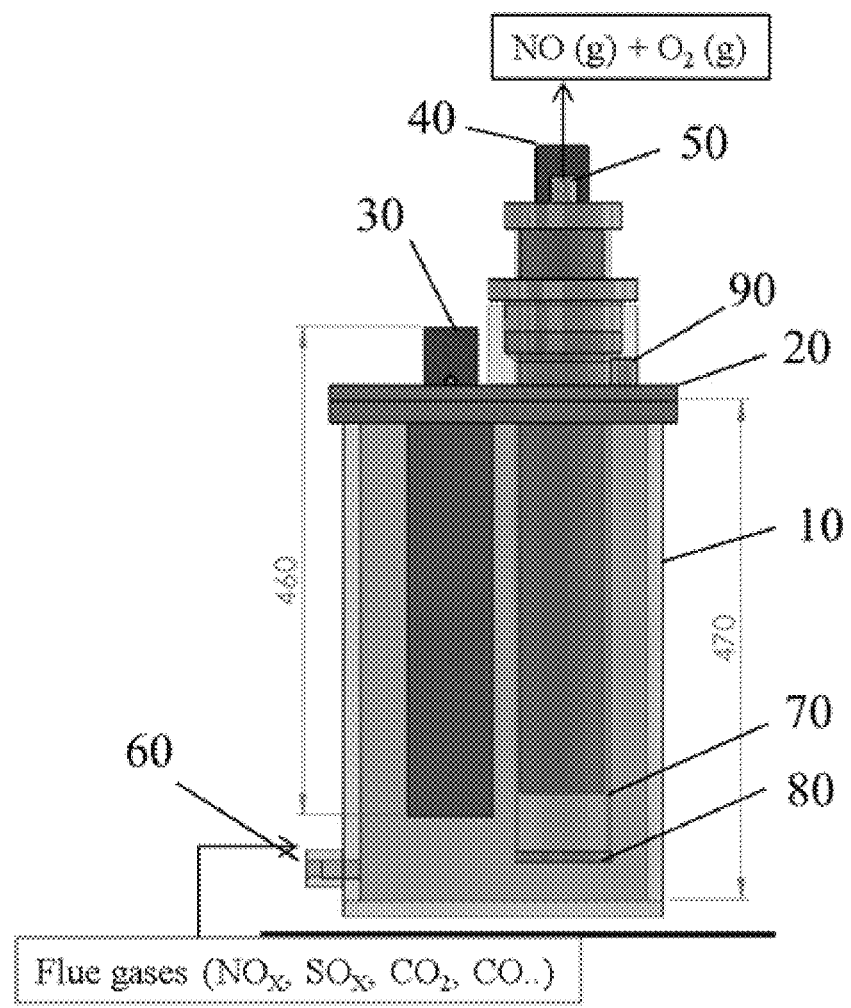
FIG. 1 illustrates an electrolysis apparatus for collecting a nitrogen compound using Fe-EDTA according to the present invention.

- 10: Reactor body
- 20: Upper reactor cover
- 30: Cathode
- 40: Anode
- 50: Nitrogen compound collector
- 60: Gas inlet
- 70: Collection tube
- 80: Porous plate
- 90: Outlet

DETAILED DESCRIPTION OF THE EMBODIMENTS

Unless otherwise defined, all technical and scientific terms used herein have the same meaning as commonly understood by a person skilled in the art to which the present invention pertains. In general, the terminology used herein is well-known and commonly used in the art.

In the present invention, a nitrogen compound collection experiment was performed by supplying exhaust gas to the electrolysis apparatus for collecting a nitrogen compound using ferric-ethylenediaminetetraacetic acid (Fe-EDTA). As a result, it was confirmed that a regeneration rate of Fe-EDTA is fast, as compared with a nitrogen compound collection method using microorganisms, thereby allowing fast nitrogen compound collection.

Therefore, according to one aspect, the present invention relates to an electrolysis apparatus for collecting a nitrogen compound, comprising (a) a reactor body comprising a compound of divalent metal ion and chelating agent therein; (b) an anode and a cathode; (c) a collection tube for collecting the nitrogen compound, comprising the anode therein; (d) a gas inlet for supplying raw material gas containing the nitrogen compound to the reactor body; and (e) an outlet for discharging gas which has been collected inside the reactor and the nitrogen compound is removed from.

The electrolysis apparatus for collecting a nitrogen compound according to the present invention will be described in detail with reference to the accompanying drawings below.

The electrolysis apparatus of the present invention includes a reactor body, an anode and a cathode, a collection tube, a gas inlet, and an outlet. In the reactor body, a compound of divalent metal ion and chelating agent is contained as an aqueous solution phase, and one side of the anode and the cathode is immersed in the aqueous solution. The other side of the anode and the cathode is disposed on the outside of the reactor body for supplying electric power, and the anode is surrounded by the collection tube, so that the nitrogen compound separated from the anode is discharged to the top of the collection tube. Besides, the gas inlet supplying raw material gas and the outlet discharging gas from which the nitrogen compound is removed are included, thereby allowing continuous operation.

In an exemplary embodiment of the present invention, the electrochemical reactions occurring in the anode and the cathode when supplying nitrogen monoxide are as follows:

$3H_2O \rightarrow 6H^+ + 3/2O_2 + 6e^-$ at anode [Equation 1]

$6Fe(II)EDTA\text{-}NO(aq) \rightarrow 6Fe(III)EDTA(aq) + 6NO(g) + 6e^-$ at anode [Equation 2]

$6H^+ + 6e^- \rightarrow 3H_2$ at cathode [Equation 3]

$6Fe(III)EDTA(aq) + 6e^- \rightarrow 6Fe(II)EDTA(aq)$ at cathode [Equation 4]

$6Fe(II)EDTA(aq) + 6NO(g) \rightarrow 6Fe(II)EDTA\text{-}NO(aq)$ [Equation 5]

In the present invention, nitrogen monoxide in exhaust gas supplied by the exhaust inlet 60 of FIG. 1 is adsorbed by a divalent ferric-ethylenediaminetetraacetic acid (Fe(II)EDTA) solution contained in the reactor body 10, thereby being present as liquid Fe(II)EDTA-NO (Equ. 5). When supplying external electric energy, water is oxidized in the anode 40 and converted into hydrogen ions, electrons and oxygen gas, and at the same time, NO-adsorbed Fe(II)EDTA, i.e., Fe(II)EDTA-NO is oxidized and converted into Fe(III)EDTA and electrons (Equ. 2), thereby separating the adsorbed NO. Herein, it is possible to purely separate NO gas without contact with exhaust gas by a glass tube surrounding the anode. Meanwhile, Fe(III)EDTA losing adsorption performance to NO receives electrons from the cathode of the reactor to be reduced to Fe(II)EDTA again, thereby being reused in collection of NO (Equ. 4 and 5). Simultaneously, in the cathode, hydrogen ions receive electrons to proceed with a reaction to produce hydrogen gas. The produced hydrogen gas is discharged to the exhaust gas outlet 90 together with exhaust gas excluding NO, and if required, may be collected.

The electrolysis apparatus according to the present invention may be characterized by further comprising a means for preparing nitric acid ($HNO_3$) using the collected nitrogen compound. In the case that the collected nitrogen compound is discharged to the air as it is, another environmental problem may arise. Therefore, it is preferred to use the collected nitrogen compound in preparation of an ammonia-based compound, nitric acid, or the like. In addition, since the nitrogen compound collected as described above is preferably nitrogen oxides, when adding a means for preparing nitric acid using the nitrogen oxides, the nitric acid may be obtained at low cost.

The electrolysis apparatus for collecting a nitrogen compound according to the present invention may further include (g) a $NO_2$ removal means to react $NO_2$ and water in raw material gas to separate nitric acid; and (h) a NO collection means to react the $NO_2$-removed raw material gas with the compound of divalent metal ion and chelating agent to separate NO and supply the NO to the reactor body.

Figure 2:
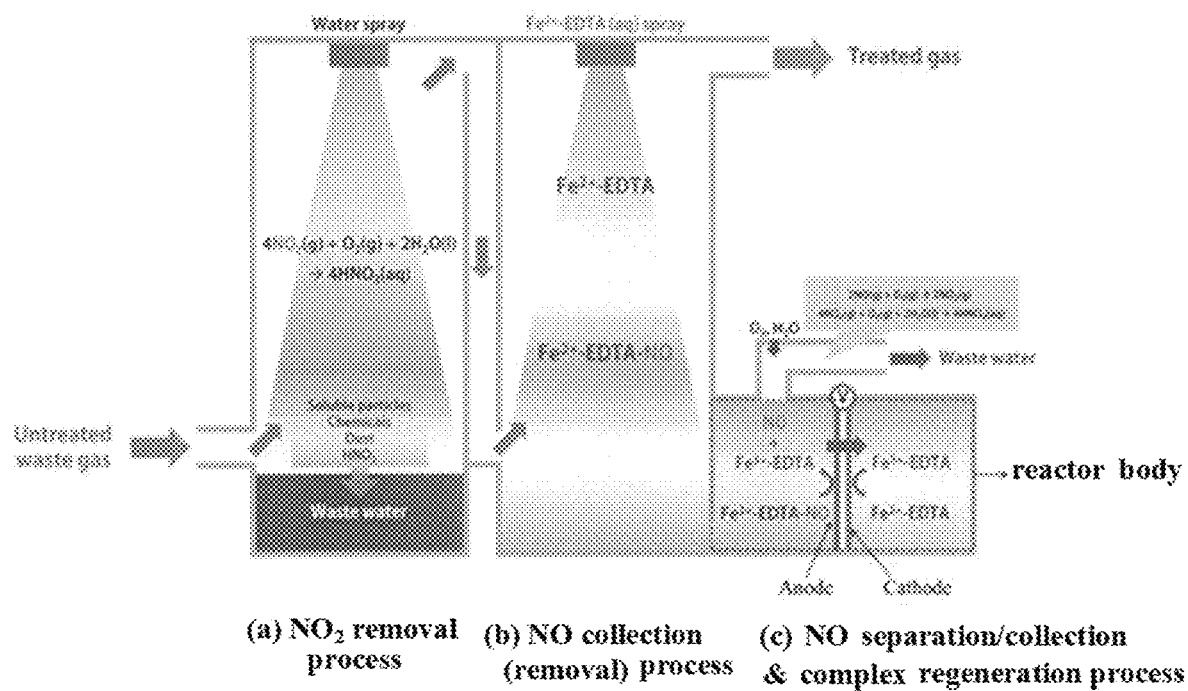
FIG. 2 is a schematic diagram of an electrolysis apparatus for collecting a nitrogen compound using Fe-EDTA according to the present invention applied to a real process, in which (a) is a $NO_2$ removal process for removing $NO_2$, (b) is a NO collection process for removing NO, and (c) is an electrolysis apparatus for collecting a nitrogen compound using Fe-EDTA.

As illustrated in FIG. 2, the raw material gas including $CO_2$, CO, $NO_x$, $SO_x$, dust and the like is introduced as the $NO_2$ removal means, and $NO_2$ accounting for about 5% of total $NO_x$ reacts with water through a water spray and is converted into nitric acid ($HNO_3$). In addition, most of dusts may be separated by contact with water.

The $NO_2$-removed raw material gas is introduced to a NO collection means. In the NO collection means, only NO is selectively collected among the raw material gas, using the characteristic of the chelating agent, Fe(II)EDTA which selectively adsorbs nitrogen monoxide (NO), through which 95% or more of NO may be removed from the raw material gas.

The raw material gas discharged from the NO collection means contains a trace amount of nitrogen monoxide, which may be supplied to the reactor body, thereby further removing the nitrogen compound.

In the present invention, as the divalent metal ion, aluminum, magnesium, potassium, copper, zinc, nickel, cobalt, manganese, lead, silver, gold or chromium may be used in addition to iron. The divalent metal ion is bonded to the chelating agent to form a compound, and this compound serves to collect the nitrogen compound. Among them, it is preferred to use ions of iron or aluminum having compatibility with the nitrogen compound, and more preferably, iron ions may be used.

In the present invention, it is characterized that the chelating agent is ethlenediamine-tetraacetic acid (EDTA). The chelating agent collectively refers to a compound binding to a metal to produce a chelating compound, and generally EDTA, 1,2-cyclohexanediaminetetraacetic acid (CyDTA), disodium nitrilotriacetic acid (NTA) and the like are used a lot. The chelating agent reacting with a metal to form a divalent compound may be used without limitation, but it is preferred to use EDTA which has excellent reactivity with a metal and may react with various metals. Therefore, the compound of divalent metal ion and chelating agent is preferably a compound of divalent iron or aluminum ion and EDTA, more preferably, a compound of divalent iron ion and EDTA.

In the present invention, the reactor may be characterized by having an upper reactor cover capable of injecting the compound of divalent metal ion and chelating agent, mounted on the upper end. The reactor may be continuously used by recirculating the compound of divalent metal ion and chelating agent, however, it is possible to newly inject the compound of divalent metal ion and chelating agent at the beginning of the reaction, or if replacement of the compound of divalent metal ion and chelating agent is needed, it is possible to perform injection and replacement using the upper cover. In addition, the upper cover may be formed on a part of the upper portion of the reactor for injection or replacement of the compound of divalent metal ion and chelating agent, however, the entire upper portion of the reactor is formed of the upper cover so that the anode, the cathode, the collection tube, the gas inlet, or gas may be formed on the cover.

In the present invention, the compound of divalent metal ion and chelating agent may be characterized by having a concentration of 10 mM-0.5 M. In the case that the concentration is 10 mM or less, the concentration of the compound of divalent metal ion and chelating agent capable of adsorbing the nitrogen compound is lowered, thereby decreasing the collection amount of the nitrogen compound, and in the case that the concentration is 0.5 M or more, the compound of divalent metal ion and chelating agent is not dissolved and is precipitated, thereby being attached to the electrode or a wall. However, since the collection amount of the nitrogen compound is proportional to the amount of the compound of divalent metal ion and chelating agent, the concentration of the compound of divalent metal ion and chelating agent is more preferably 0.5 M.

In the present invention, the anode may be characterized by being composed of a mixture of one or more conductive metals selected from the group consisting of graphite, platinum, titanium, nickel and gold, and one or more catalysts selected from the group consisting of platinum, ruthenium, osmium, palladium, iridium, carbon, and transition metals, and the cathode may be characterized by being composed of a mixture of one or more conductive metals selected from the group consisting of graphite, platinum, titanium, nickel, gold, iron, copper and aluminum, and one or more catalysts selected from the group consisting of platinum, ruthenium, osmium, palladium, iridium, carbon and transition metals. As the electrode materials of the anode and the cathode, any material may be used as long as it is a mixture of a conductive metal and a catalyst metal, however, iron or aluminum may not be used, which proceeds with an oxidation reaction when electric energy is introduced to the electrode material of the anode. In addition, as the catalyst material, a Pt/C catalyst in which platinum is attached to a carbon support is preferably used.

In the present invention, it is characterized in that a porous plate is provided on the lower portion of the collection tube. The collection tube may be manufactured of glass for collecting the nitrogen compound produced in the anode. Therefore, for contact of the anode disposed inside the collection tube with the compound of divalent metal ion and chelating agent, it is preferred to provide a porous plate on the lower portion of the collection tube. In addition, on an upper portion of the collection tube, a nitrogen compound collector which discharges the nitrogen compound separated from the anode to the outside is provided, and thus, it is preferred to discharge the separated nitrogen compound to the outside.

In the present invention, it is characterized in that the nitrogen compound is nitrogen oxides ($NO_x$). Among the nitrogen compounds, the material affecting the atmosphere is nitrogen oxides, among which nitrogen monoxide having high reactivity affects the atmosphere the most. Therefore, the nitrogen compound may be preferably nitrogen oxides ($NO_x$), and more preferably nitrogen monoxide (NO).

According to another aspect, the present invention relates to a method of collecting a nitrogen compound using the electrolysis apparatus, the method comprising (i) adsorbing the nitrogen compound to the compound of divalent metal ion and chelating agent by supplying raw material gas comprising a nitrogen compound to a reactor containing a compound of divalent metal ion and chelating agent; (ii) collecting discharged nitrogen compound by supplying electricity to an anode and a cathode, oxidizing the nitrogen compound-adsorbed compound of divalent metal ion and chelating agent to a compound of trivalent metal ion and chelating agent through an oxidation reaction in the anode and discharging the nitrogen compound; (iii) recovering collected nitrogen compound; and (iv) reducing oxidized compound of trivalent metal ion and chelating agent to the compound of divalent metal ion and chelating agent by electrons produced in the cathode.

It is as described above that the compound of divalent metal ion and chelating agent bonded to the nitrogen compound is oxidized on the anode to separate the nitrogen compound and converted to the compound of trivalent metal ion and chelating agent, and then is reduced on the cathode to be regenerated as the compound of divalent metal ion and chelating agent.

The method of collecting a nitrogen compound according to the present invention may be characterized by further including a step of (v) preparing nitric acid ($HNO_3$) using the collected nitrogen compound. The collected nitrogen compound may cause another pollution, if discharged to the outside, and is difficult to be stored as a gaseous phase, and thus, it is preferred that the collected nitrogen compound is converted to another compound and treated. The nitrogen oxides react with water to produce nitric acid, and thus, it is preferred to prepare nitric acid using the collected nitrogen compound. In addition, in the case of preparing nitric acid by the above method, it is possible to prepare the nitric acid at low cost, as compared with the conventional preparation method of nitric acid.

The method of collecting a nitrogen compound according to the present invention may further include: ① a $NO_2$ removal step to spray water to the raw material gas to react $NO_2$ in the raw material gas and water to obtain nitric acid; and ② a NO collection step to react the $NO_2$-removed raw material gas with the compound of divalent metal ion and chelating agent to separate NO, prior to the step (i).

As illustrated in FIG. 2, for removing nitrogen oxides by directly supplying the raw material gas including $CO_2$, CO, $NO_x$, $SO_x$, dusts and the like, it is preferred to subject the raw material gas to pretreatment before supplying the raw material, since the concentration of the nitrogen oxides in the raw material gas is high, and the compound of divalent metal ion and chelating agent, the anode and the cathode may be damaged by other components.

EXAMPLES

Hereinafter, the present invention will be described in more detail by the following Examples. These Examples are provided only to illustrate the present invention, and it will be evident to a person skilled in the art that the scope of the present invention is not construed to be limited to those Examples.

Example 1: Collection of Nitrogen Monoxide Using Divalent Fe-EDTA

A nitrogen monoxide collection experiment proceeded using the electrolysis apparatus including the reactor body, the anode and the cathode, the collection tube, the gas inlet, and the outlet.

A divalent Fe ion and EDTA were injected to the inside of the reactor using the upper cover on the upper portion of the reactor body, and then the cover was sealed. Thereafter, exhaust gas was supplied to the gas inlet, and electricity was supplied to the anode and the cathode, thereby proceeding with the experiment.

As a result of proceeding with the experiment, it was confirmed that the nitrogen monoxide was detected at least in the outlet, and most of the nitrogen monoxide was separated and discharged through the nitrogen compound collector in the upper portion of the collection tube.

Example 2: Actual Exhaust Gas Treatment Using Electrolysis Apparatus for Collecting Nitrogen Compound An actual exhaust gas treatment process was performed using the electrolysis apparatus for collecting a nitrogen compound, manufactured in Example 1. As illustrated in FIG. 2, the exhaust gas including $CO_2$, CO, $NO_x$, $SO_x$, dust and the like was introduced as the $NO_2$ removal means, and $NO_2$ accounting for about 5% of total $NO_x$ reacted with water through a water spray and was converted into nitric acid ($HNO_3$). In addition, most of dusts were separated by contact with water.

The exhaust gas from which $NO_2$ and dusts were removed was introduced to the NO collection means. The NO collection means selectively collects only NO in the exhaust gas, using the characteristic of the chelating agent, Fe(II) EDTA selectively adsorbing nitrogen monoxide (NO), from which 95% or more of NO was removed from the exhaust gas.

The exhaust gas passing through the NO collection means included a trace amount of nitrogen monoxide, and this was supplied to the electrolysis apparatus for collecting a nitrogen compound of Example 1 to remove the nitrogen compound therefrom.

The present invention has been described in detail in specific parts, and it is obvious that such specific technique is only a preferred embodiment to a person skilled in the art, without limiting the scope of the present invention thereby. Thus, the substantial scope of the present invention will be defined by the appended claims and their equivalents.

INDUSTRIAL APPLICABILITY

The electrolysis apparatus for collecting a nitrogen compound according to the present invention uses a minimum of expensive rare earth catalysts, and performs regeneration of the adsorbent simultaneously, and thus, may efficiently collect the nitrogen compound.

What is claimed is:

1. An electrolysis apparatus for collecting a nitrogen compound, comprising:
   (a) a reactor body comprising a compound of divalent metal ion and chelating agent therein;
   (b) an anode and a cathode;
   (c) a collection tube for collecting the nitrogen compound, comprising the anode therein;
   (d) a gas inlet for supplying raw material gas containing the nitrogen compound to the reactor body;
   (e) an outlet for discharging gas which has been collected inside the reactor and from which the nitrogen compound is removed; and
   (f) a pretreatment vessel arranged to receive a gas containing nitrogen oxides and to contact said gas containing nitrogen oxides with water in the pretreatment vessel to yield (i) nitric acid ($HNO_3$) and (ii) gas containing the nitrogen compound as said raw material gas.

2. The electrolysis apparatus for collecting a nitrogen compound of claim 1, further comprising:
   (g) the pretreatment vessel being arranged to receive a gas containing $NO_2$ and the nitrogen compound, for reacting $NO_2$ and water to yield $NO_2$-removed raw material gas containing the nitrogen compound and separating nitric acid wherein the nitrogen compound comprises NO;
   (h) a NO collection vessel arranged to receive the $NO_2$-removed raw material gas from the pretreatment vessel, and to contact the $NO_2$-removed raw material gas with the compound of divalent metal ion and chelating agent to selectively adsorb NO by the compound of divalent metal ion and chelating agent, and thereby remove NO from the $NO_2$-removed raw material gas to yield a treated gas that is discharged from the NO collection vessel; and (i) a NO separation and regeneration vessel, arranged to receive the compound of divalent metal ion and chelating agent with selectively adsorbed NO, for electrochemical reaction therein to separate the NO from the compound of divalent metal ion and chelating agent, and regenerate the compound of divalent metal ion and chelating agent, so that the separated NO is discharged from the NO separation and regeneration vessel and supplied to the reactor body as said raw material gas.

3. The electrolysis apparatus for collecting a nitrogen compound of claim 1, wherein the divalent metal ion is iron, aluminum, magnesium, potassium, copper, zinc, nickel, cobalt, manganese, lead, silver, gold or chromium.

4. The electrolysis apparatus for collecting a nitrogen compound of claim 1, wherein the chelating agent is ethylenediamine tetraacetic acid (EDTA).

5. The electrolysis apparatus for collecting a nitrogen compound of claim 1, wherein the compound of divalent metal ion and chelating agent is Fe(II)EDTA.

6. The electrolysis apparatus for collecting a nitrogen compound of claim 1, wherein the reactor has an upper reactor cover mounted on the upper end, capable of injecting the compound of divalent metal ion and chelating agent.

7. The electrolysis apparatus for collecting a nitrogen compound of claim 1, the compound of divalent metal ion and chelating agent has a concentration of 10 mM-0.5 M.

8. The electrolysis apparatus for collecting a nitrogen compound of claim 1, wherein the anode is composed of a mixture of one or more conductive materials selected from the group consisting of graphite, platinum, titanium, nickel and gold, and one or more catalysts selected from the group consisting of platinum, ruthenium, osmium, palladium, iridium, carbon and transition metals.

9. The electrolysis apparatus for collecting a nitrogen compound of claim 1, wherein the cathode is composed of a mixture of one or more conductive materials selected from the group consisting of graphite, platinum, titanium, nickel, gold, iron, copper and aluminum, and one or more catalysts selected from the group consisting of platinum, ruthenium, osmium, palladium, iridium, carbon and transition metals.

10. The electrolysis apparatus for collecting a nitrogen compound of claim 1, wherein a porous plate is provided on a lower portion of the collection tube.

11. The electrolysis apparatus for collecting a nitrogen compound of claim 1, wherein the nitrogen compound is nitrogen oxide ($NO_x$).

12. The electrolysis apparatus for collecting a nitrogen compound of claim 11, wherein the nitrogen oxide is nitrogen monoxide (NO).

13. A method of collecting a nitrogen compound using the electrolysis apparatus of claim 1, comprising:
(i) adsorbing the nitrogen compound to the compound of divalent metal ion and chelating agent by supplying raw material gas comprising a nitrogen compound to a reactor containing a compound of divalent metal ion and chelating agent;
(ii) collecting discharged nitrogen compound by supplying electricity to an anode and a cathode, oxidizing the nitrogen compound-adsorbed compound of divalent metal ion and chelating agent to a compound of trivalent metal ion and chelating agent through an oxidation reaction in the anode and discharging the nitrogen compound;
(iii) recovering collected nitrogen compound; and (iv) reducing oxidized compound of trivalent metal ion and chelating agent to the compound of divalent metal ion and chelating agent by electrons produced in the cathode.

14. The method of collecting a nitrogen compound of claim 13, wherein the nitrogen compound is nitrogen oxide ($NO_x$).

15. The method of collecting a nitrogen compound of claim 14, wherein the nitrogen oxide is nitrogen monoxide (NO).

16. The method of collecting a nitrogen compound of claim 13, further comprising a step of (v) preparing nitric acid ($HNO_3$) using collected nitrogen compound.

17. The method of collecting a nitrogen compound of claim 13, further comprising, prior to the step (i)
a $NO_2$ removal step of reacting $NO_2$ in the raw material gas and water to obtain nitric acid ($HNO_3$) by, spraying water to the raw material gas in the pretreatment vessel; and
wherein the adsorbing step (i) comprises a NO collection step of reacting the $NO_2$-removed raw material gas with the compound of divalent metal ion and chelating agent and separating NO.

* * * * *